United States Patent [19]

Becker et al.

[11] Patent Number: 5,021,043
[45] Date of Patent: Jun. 4, 1991

[54] METHOD AND CATHETER FOR DILATATION OF THE LACRIMAL SYSTEM

[75] Inventors: Bruce B. Becker, Encino, Calif.; William A. Berthiaume, Hudson, Mass.

[73] Assignee: C. R. Bard, Inc., Murray Hill, N.J.

[21] Appl. No.: 405,766

[22] Filed: Sep. 11, 1989

[51] Int. Cl.$^5$ .............................................. A61M 31/00
[52] U.S. Cl. ...................................... 604/49; 128/898; 604/96; 606/192
[58] Field of Search ................................. 604/27–28, 604/49, 54, 96–103, 164, 264, 294; 128/658, 898; 606/192–194

[56] References Cited

U.S. PATENT DOCUMENTS

| | | | |
|---|---|---|---|
| 2,154,968 | 4/1939 | Alkio | 128/348 |
| 3,726,284 | 4/1973 | Parker | 128/350 |
| 3,948,272 | 4/1976 | Guibor | 128/350 |
| 4,305,395 | 12/1981 | Martinez | 128/348 |
| 4,380,239 | 4/1983 | Crawford et al. | 604/28 |
| 4,578,058 | 3/1986 | Grandon | 604/27 |
| 4,658,816 | 4/1987 | Ector Jr. | 128/303 |
| 4,660,546 | 4/1987 | Herrick et al. | 128/1 |
| 4,671,291 | 6/1987 | Wilson | 128/658 |
| 4,684,363 | 8/1987 | Ari et al. | 604/98 |
| 4,762,129 | 8/1988 | Bonzel | 604/96 X |
| 4,793,359 | 12/1988 | Sharrow | 604/96 X |
| 4,798,586 | 1/1989 | Stevens | 604/96 |
| 4,848,344 | 7/1989 | Sos et al. | 604/96 X |

OTHER PUBLICATIONS

Aguirre et al., "Inflatable Catheter for Dacryocystorhinostomy", Arch. Ophthalmol., vol. 106, pp. 692–694, May 1988.

Becker et al., "Balloon Catheter Dilatation in Lacrimal Surgery", Opthalmic Surgery, vol. 20, No. 3, pp. 193–198, Mar. 1989.

*Primary Examiner*—C. Fred Rosenbaum
*Assistant Examiner*—Corrine Maglione
*Attorney, Agent, or Firm*—Wolf, Greenfield & Sacks

[57] ABSTRACT

A dilatation catheter having an inflatable member and a method of using same to restore patency to an obstructed portion of the lacrimal system. The catheter is inserted into the lacrimal system and its inflatable member is positioned in the obstructed portion. The inflatable member is inflated to dilate the obstructed portion to restore patency to the lacrimal system. Preferably, the catheter includes one or more visually perceivable markers having a known spaced relationship to one of the ends of the inflatable member. Positioning of the inflatable member is assisted by aligning the marker relative to an opening into the lacrimal system.

52 Claims, 4 Drawing Sheets

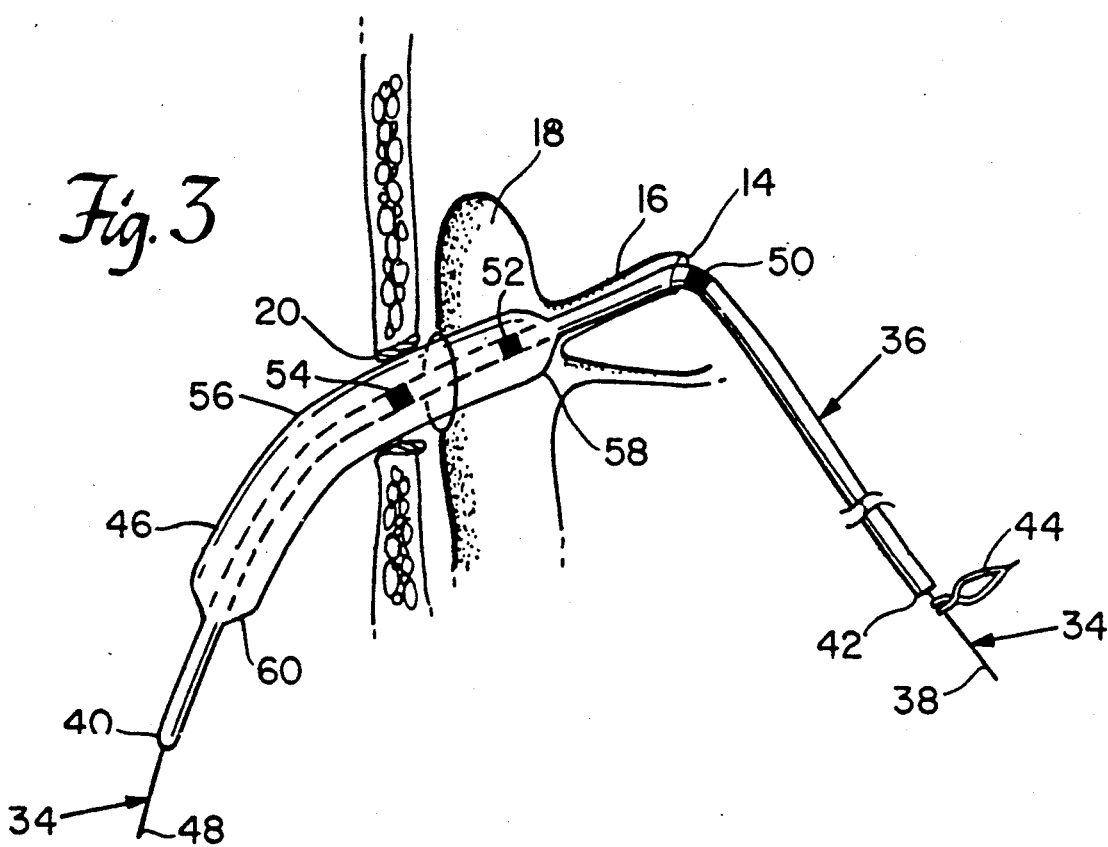
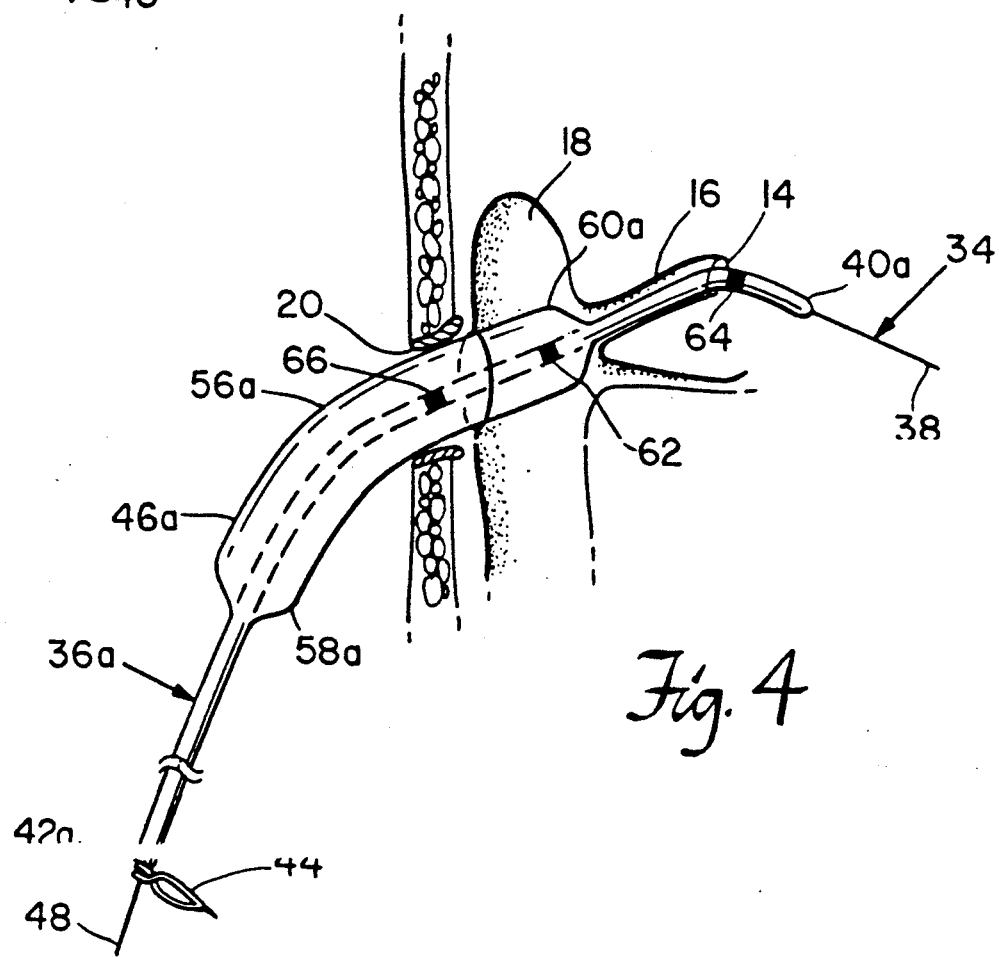

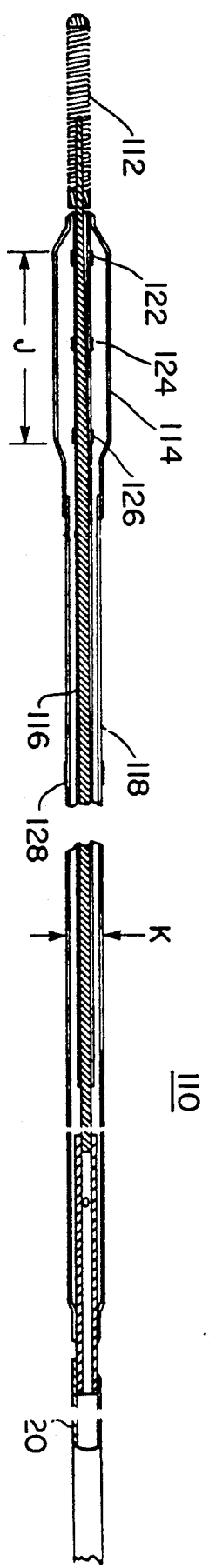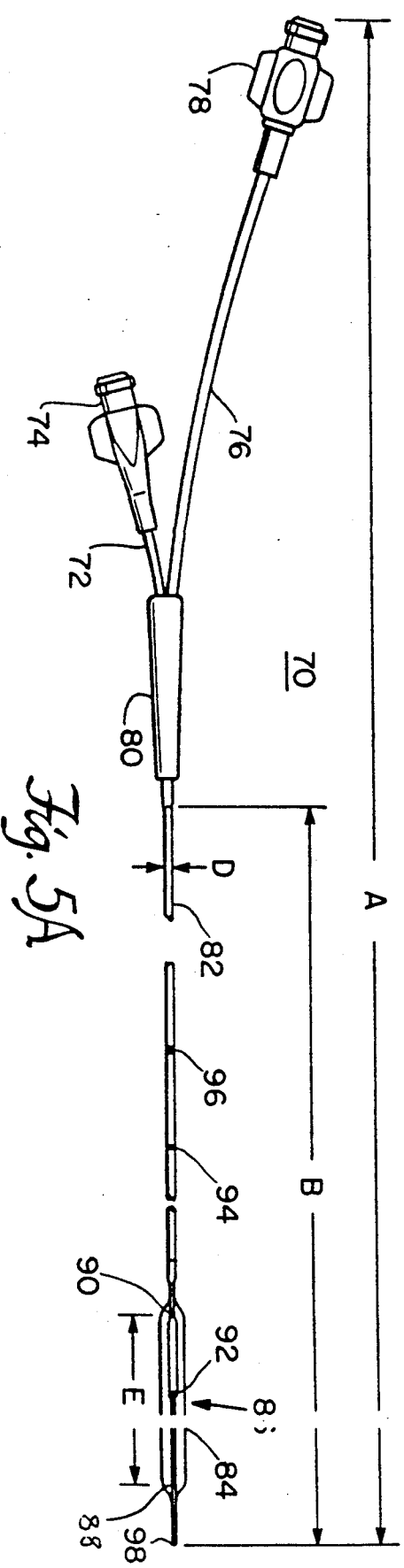

METHOD AND CATHETER FOR DILATATION OF THE LACRIMAL SYSTEM

FIELD OF THE INVENTION

This invention relates to a method of restoring patency to an obstructed portion of the lacrimal system using a dilatation catheter, and to such a catheter having visually perceptible markings to enable alignment of an inflatable member with the obstructed portion of the lacrimal system.

BACKGROUND OF THE INVENTION

The excessive overflow of tears down a cheek due to an obstruction in the nasolacrimal drainage system is a relatively common problem. The excessive overflow, referred to epiphora or "watering eye", is often accompanied by infection with attendant inflammatory reaction.

Normally, tears are drained from the eye through the nasolacrimal drainage system (hereinafter the lacrimal system) which includes an upper and lower canaliculus each of which communicates with its respective eyelid through an opening known as the punctum. The other ends of the canaliculi join together at the upper end of the nasolacrimal duct. The upper end of the nasolacrimal duct also communicates with the lacrimal sac. The lower end of the nasolacrimal duct opens into the nose.

Presently, minor obstructions of the lacrimal system commonly are treated by dilatation using metal probes. More severe obstructions of the nasolacrimal duct are treated by performing a dacryocystorhinostomy (DCR) during which the lacrimal sac is surgically connected with the nasal cavity. DCR is a relatively major surgical procedure involving making an incision next to the bridge of the nose near the lacrimal sac, breaking through the bone to access the nose, and cutting away a portion of the lacrimal sac. The newly created opening into the nose is referred to as the ostium.

As many as one in ten DCR operations fail to due subsequent closure of the ostium. The ostium can be reopened surgically, but few patients wish to undergo the trauma of a second surgery which involves the excising of additional tissue, anesthesia, and subsequent packing of the nose with absorbent material for two to three days following the surgery.

A number of techniques presently are attempted to avoid the trauma of a second surgery. Dilatation of the ostium with a metal probe, intranasal dilatation with a muscle hook, and dilatation with a knotted suture are used with varying degrees of success. A silicone tube frequently is attached to the probe so that the silicone tubing is installed in the lacrimal system to serve as a stent in an attempt to maintain patency of the ostium. However, the canaliculus is typically only 0.5–1.0 mm in diameter and the internal diameter of the stent is therefore relatively small and ineffective. These techniques usually do not succeed in reopening the ostium for a sufficient period of time. Often, the tissue surrounding the ostium simply recloses after the probe is removed, even when the silicone tubing stent is present.

One such stent is a silicone catheter with an inflatable balloon which is positioned within the patient's lacrimal sac. The catheter maintains communication between the lacrimal sac and the nose. The balloon is of a sufficient size to prevent postoperative migration of the catheter to the nasal fossa. After the patient is healed, the balloon is deflated and the catheter is removed by pulling it through the patient's nostril. In other words, the balloon is not used for dilatation, but simply serves as a retaining element for the stent.

Obstruction of a canaliculus can also occur. Various solid, rigid instruments have been used to dilate a canalicular stenosis. Commonly, a rigid metal probe is used followed by silicone intubation as a stent. However, the number of failures is high and an operation called a conjunctivodacryocystorhinostomy (CDCR) must frequently be performed. The CDCR involves bypassing the lacrimal system by surgically creating an opening from the eye into the nose. A short pyrex tube is then installed so that it creates a passage from the eye straight into the nose. This procedure is poorly tolerated by most patients. Further, the CDCR can become obstructed, particularly if the pyrex tube becomes dislodged.

Additionally, obstruction of the punctum is very common. Again, the punctal stenosis is usually treated with a solid metal probe with varying degrees of success.

In a separate subject area, balloon catheter dilatation has been used to treat stenotic blood vessels, urinary tract obstruction, and strictures of the gastrointestinal tract. In percutaneous transluminal coronary angioplasty, for example, a guidewire is maneuvered along a selected coronary artery until an occlusion is reached. A balloon catheter is then advanced over the guidewire by pushing on the proximal end of the balloon catheter. After the balloon is positioned within the occlusion, it is inflated to dilatate the occlusion. Frequently, the first balloon catheter is withdrawn and a second, larger-diameter balloon catheter is positioned to perform a subsequent dilatation. No suggestion has been made by others to use balloon catheters in the treatment of an obstructed lacrimal system by performing dilatation of the obstruction.

SUMMARY OF THE INVENTION

The method of the invention involves restoring patency to an obstructed portion of the lacrimal system of a patient by performing dilatation using an inflatable member carried by a catheter. The method includes providing a catheter having an inflatable member, inserting the catheter into the lacrimal system, and positioning the inflatable member proximate to the obstructed portion of the lacrimal system. The inflatable member is inflated to dilate the obstructed portion to restore patency to the lacrimal system. This technique obviates the need for surgery with its attendant trauma.

In a preferred technique, the provided catheter includes a visually perceivable marker having a known spaced relationship to one of the ends of the inflatable member, and positioning the inflatable member includes aligning the marker relative to an opening in the lacrimal system, such as a punctum, the opening of the nasolacrimal duct into the nose, or an ostium formed between the nose and the lacrimal sac. The provided catheter in one embodiment includes a lumen for receiving a guidewire. Initially, a probe is passed through the lacrimal system to determine a path between the first and second openings through the obstruction, after which a sleeve such as an angiocath having a relatively rigid core is advanced along the same path after the probe is withdrawn. The core is then withdrawn while leaving the sleeve in position. The guidewire is then advanced through the sleeve, and the sleeve is withdrawn. The proximal end of the catheter is interlocked relative to the guidewire, and the guidewire is pulled to draw the inflatable member into the lacrimal system. The inflatable member is then inflated and deflated during one or more periods of time to dilatate the obstruction in the lacrimal system.

Alternatively, the catheter does not utilize a separate guidewire and the catheter body has a distal segment which is more flexible than a proximal segment. Preferably, the distal segment includes a slender, flexible wire which serves as a core member and a spring coil tip disposed about the distal portion of the core member.

It is also desirable for the catheter to include a lubricious coating to facilitate inserting the catheter into the lacrimal system. The coating may be a silicone coating bonded to the catheter, or may be topically applied to the catheter body and the inflatable member.

The dilatation catheter of the invention has one or more visually perceivable markers having a known spaced relationship from one of the distal end and the proximal end of the center region of an inflatable member. These markers enable alignment of the inflatable member with the obstructed portion of the lacrimal system to be dilated. The arrangement of the markings and the techniques of utilizing the markings varies according to the location of the obstructed portion to be dilated. For treating a failed dacryocystorhinostomy (DCR), for example, a catheter according to the invention includes a first visually perceivable marker spaced 9-13 mm proximal to the proximal end of the center region such that when the catheter is inserted through a punctum and associated canaliculus and then through an ostium formed between the nose and the lacrimal sac, the first marker is aligned relative to the punctum to position the inflatable member. Preferably, the inflatable member is a translucent balloon and a second visually perceivable marker is located beneath the balloon at a distance of 4-6 mm distal to the proximal end of the center region to enable alignment of the second marker relative to the ostium. Alternatively, the catheter is inserted through the ostium and then through the canaliculus and its associated punctum, and the first visually perceivable marker is spaced 9-13 mm distal to the distal end of the center region, and a second visually perceivable marker is located beneath the balloon at a distance of 4-6 mm proximal to the distal end of the center region. The first marker is aligned relative to the punctum and the second marker is aligned relative to the ostium to position the balloon to effectively dilate the ostium.

To dilate the nasolacrimal duct, the catheter is inserted through a punctum and associated canaliculus and then advanced through the nasolacrimal duct. A first visually perceivable marker is located beneath the inflatable member at a distance of 4-6 mm proximal to the distal end of the center region for alignment of the first marker relative to the opening of the nasolacrimal duct into the nose. A second visually perceivable marker is spaced 9-16 mm proximal to the proximal end of the center region for alignment relative to the punctum. The second marker is preferably located 9-11 mm from the proximal end of the center region and the catheter further includes a third marker located 14-16 mm proximal to the proximal end of the center region. The second and third markers are then aligned relative to the punctum. If the balloon is not sufficiently long to occupy the entire nasolacrimal duct, a first dilatation is performed after the first marker is aligned relative to the opening of the nasolacrimal duct, and thereafter a second dilatation is performed after aligning the second and third markers relative to the punctum after the catheter is withdrawn toward the canaliculus.

During yet another procedure according to the invention, the catheter is inserted through a punctum and associated canaliculus for dilatation of the canaliculus. A first visually perceivable marker is spaced 9-16 mm proximal to the distal end of the center region for alignment relative to the punctum. The catheter and method according to this invention can also be used for dilatation after conjunctivodacryocystorhinostomy (CDCR) and for dilatation of the punctum. These techniques provide successful dilatation without the need for surgery and its potential complications. The methods according to the invention can be used to restore patency to a failed surgical procedure, or can be used as a primary treatment to treat the obstruction without requiring any surgery.

It is therefore an object of the invention to provide a more effective procedure for restoring patency to a obstructed lacrimal system.

It is a further object of this invention to provide a less traumatic technique for correcting a failed DCR.

Yet another object of this invention is to provide a less invasive primary treatment as an alternative to DCR.

A still further object of the invention is to provide such a technique which avoids surgery.

A still further object of the invention is to provide a dilatation catheter for use in the treatment of obstructed lacrimal ducts.

A further object of the invention is to provide such a catheter having one or more visually perceivable markers which readily enable alignment of an inflatable member with the obstruction.

BRIEF DESCRIPTION OF THE DRAWINGS

FIG. 3 is a schematic representation of the alignment of a dilatation catheter according to the invention with features of the lacrimal system;

FIG. 4 is a schematic view of an alternative method according to this invention in which the catheter is pulled into the lacrimal system through the nose;

FIG. 5A is a schematic view of a dilatation catheter according to the invention;

FIG. 6 is a schematic view of an alternative dilatation catheter according to this invention which does not require a separate guidewire.

DESCRIPTION OF THE ILLUSTRATIVE EMBODIMENT

Dilatation by a method according to the invention of an obstruction in the nasolacrimal drainage system, hereinafter the lacrimal system, can be accomplished without surgery by providing a catheter having an inflatable member, inserting the catheter into the lacrimal system, and positioning the inflatable member proximal to the obstructed portion of the lacrimal system. The inflatable member is then inflated to dilate the obstructed portion to restore patency to the lacrimal system. This technique accomplishes much greater dilatation than that possible using a metal probe, a muscle hook, a knotted suture, or other attempts to restore patency without involving surgery.

The dilatation catheter and method according to the invention can be used to restore patency to the ostium formed between the nose and the nasolacrimal sac after a failed dacryocystorhinostomy (DCR), or for treating obstructions of the nasolacrimal duct, the canaliculus, the punctum, or combinations thereof within the lacrimal system.

The dilatation catheter and method provide an advantageous technique for accessing the lacrimal system through openings which are quite small. The punctum typically has an internal diameter of 0.5 mm and a length of approximately 1 mm. A canaliculus typically has a diameter of 0.5 mm in a relaxed, unexpanded state and a length of 10-12 mm. The artificial ostium formed during surgery usually has a diameter of approximately 2 mm and a length of 2 or more mm. The nasolacrimal duct is approximately 17 in length and has an inner diameter of 0.5-1 mm. The maximum diameter of the nasolacrimal duct is established by the diameter of the bone passageway, which is typically 3-4 mm in diameter.

Figure 1:
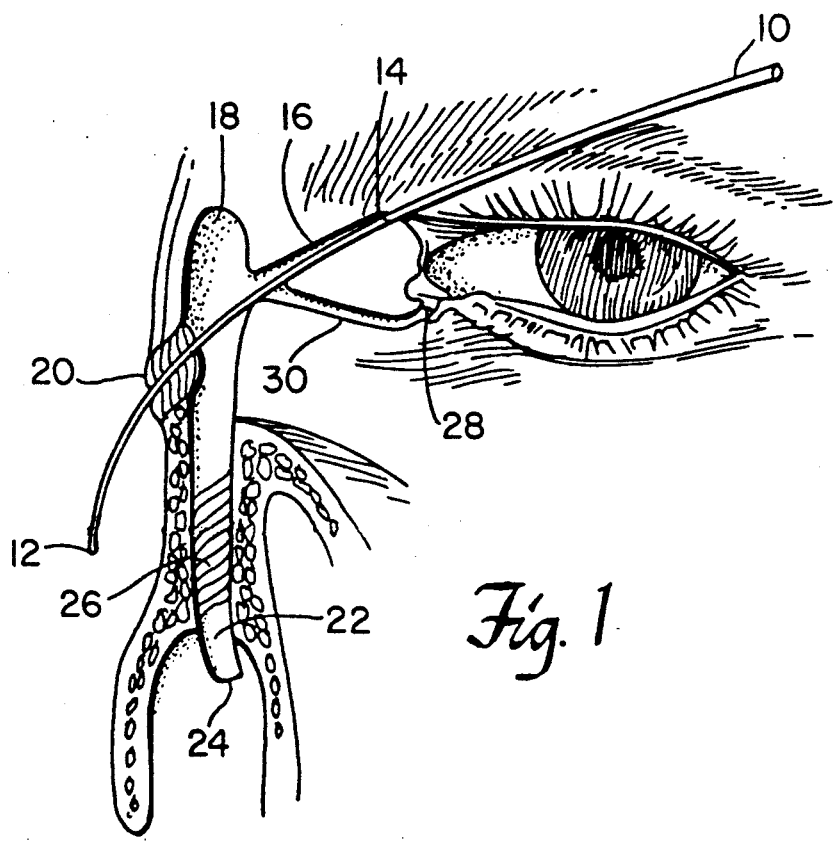
FIG. 1 is a schematic, partial cross-sectional view of a patient with an obstructed nasolacrimal duct and an obstructed ostium through which a metal probe is passed during the method of the invention.
Figure 2:
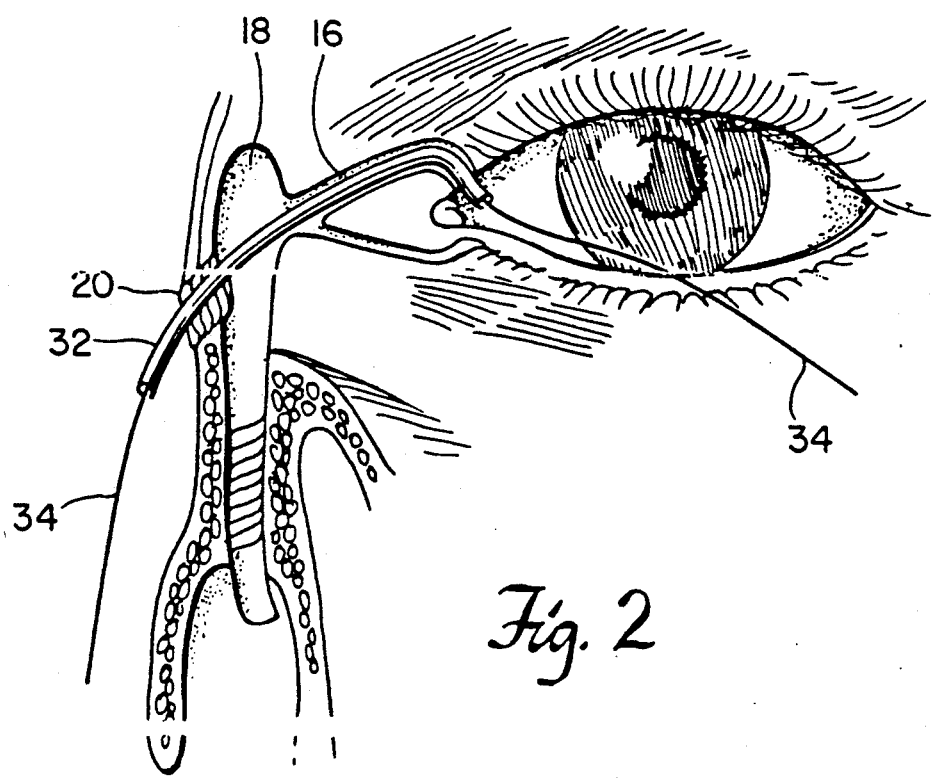
FIG. 2 is a similar view showing an angiocath sleeve and guidewire positioned within the lacrimal system according to the invention.

Dilatation of an ostium after a failed DCR is illustrated in FIGS. 1-3. Preferably, irrigation and postoperative dye testing are performed after the failed DCR and before and after catheter dilatation to confirm the need for dilatation and the success of the procedure. Postoperative dye testing can be performed by placing 2% fluorescein dye in the eye and examining the nose for presence of dye.

The patient is prepared before the dilatation procedure by applying a combination of topical and infiltration anesthesia. For example, topical 0.5% proparacaine is applied to the eye, and topical 4% lidocaine and 0.5% phenylephrine spray is delivered to the nose. A nerve block may be delivered to the anterior ethmoidal and infratrochlear nerves by injecting a 50:50 mixture of 2% lidocaine and 0.5% bupivicaine through the medial orbit. Oral or intravenous sedation may also be used.

Preferably, the insertion of a dilatation catheter according to the invention is preceded by a probe 10 such as the metal rod shown in FIG. 1. The probe 10 is approximately 0.5 mm (0.02 inch) in diameter and is moderately flexible. The distal end 12 of the probe 10 is inserted into the upper punctum 14 and passed through the upper canaliculus 16 into the lacrimal sac 18. The distal tip 12 is then inserted through the occluded ostium 20 and into the nose. The ostium was previously established during a DCR in an attempt to provide an alternative path for the drainage of tear because the normal path through the nasolacrimal duct 22 and its opening 24 into the nose is blocked by occlusion 26.

The probe 10 is alternatively advanced through lower punctum 28 and its associated lower canaliculus 30. In either case, use of the probe 10 allows the physician to determine the optimal insertion angle and proper maneuvering required to pass through the occluded ostium 20.

The probe is then withdrawn and a sleeve 32 is inserted as shown in FIG. 2. One such sleeve is a 20 gauge angiocath available from Deseret Medical, Inc. The angiocath has a sleeve formed of teflon which is approximately 2 inches long and 1.1 mm (0.043 inch) in diameter. This angiocath further includes a metal core whose tip is cut and filed until it is blunt and flush with the end of the sleeve. The sleeve 32 is passed through the canaliculus 16, the lacrimal sac 18, and the ostium 20 in the same fashion as the probe. The sleeve 32 is visualized through the nose and is positioned such that there is a 5-10 mm clearance between it and the floor of the nose. The metal core is withdrawn.

A guidewire 34 is then threaded through the sleeve 32 and into the nose. The guidewire 34 is drawn out of the nose by engaging it with a small muscle hook or grasping it with a hemostat to bring it out through the external nare. The sleeve 32 is then withdrawn while leaving the guidewire in place. Use of the sleeve 32 is optional but is desirable when passing through a very narrow obstruction through which the guidewire alone cannot readily be advanced. A preferred guidewire is the "Hyberflex" guidewire, catalog no. 004795 available from USCI, a division of C. R. Bard, Inc. This guidewire has a diameter of 0.36 mm (0.014 inch) and is coated with a silicone "Propel" coating.

After the guidewire 34 is installed and the sleeve 32 is withdrawn, a catheter 36 according to the invention is advanced over the distal end 38 of the guidewire 34 until the distal end 40 of the catheter 36 is positioned near the punctum 14. The catheter 36 is then interlocked with the guidewire 34 near the proximal end 42 of the catheter 36 by clampinq a hemostat 44 onto the guidewire 34. The hemostat 44 is a standard mosquito hemostat such as available from the V. Mueller Company. The inflatable member 46, in a deflated condition, is drawn into the lacrimal system by pulling on the distal end 48 of the guidewire 34. In other words, instead of pushing on the proximal end 42 of the catheter 36 to advance it into position, as is done during conventional angioplasty, the catheter is drawn into position by pulling on the guidewire.

The dilatation catheter 36 according to the invention includes visually perceivable markers 50, 52 and 54 which assist in the positioning of the inflatable member 46. The markers 50, 52 and 54 are established by permanent indelible ink which is placed directly on the exterior of the shaft of the catheter 36. The inflatable member 46 is translucent so that the markers 52, 54 which underlie the balloon can be seen. The term "translucent" is intended in its broadest sense to cover both translucent and transparent materials such that the markers can be seen through the inflatable member. One such translucent material is polyethylene terephthalate. Other acceptable materials are polyvinyl chloride or Surlyn, both of which are also translucent materials. The inflatable member 46 is a balloon 3-6 mm in diameter and 5-10 mm in length, preferably 3.5-5.5 mm in diameter and 6-8 mm in length, for use to expand the ostium 20, although a longer balloon is acceptable as shown for the inflatable member 46, FIG. 3, which is approximately 20 mm in length. One such balloon catheter is the "Miniprofile" catheter, catalog no. 006480 from USCI, having a 3.5 mm diameter balloon which has a deflated profile of 0.94 mm (0.037 inch).

The inflatable member 46 has a center region 56 which is the full-diameter region upon inflation. The proximal end of the center region 56 is attached to tapered proximal portion 58 and the distal end of the center region 56 is attached to a tapered distal region 60.

The marker 52 is aligned with the proximal end of the center region 56, and the marker 54 is spaced 4-6 mm, preferably 5 mm, distal to the end marker 52. The catheter shaft is illustrated extending within the inflatable member 46 by dashed lines. The marker 50, referred to as an insertion or exit marker, is located 9-13 mm, and preferably 10 mm, proximal to the end marker 52. The insertion marker 50 is aligned relative to the ostium 14 and the inflation marker 54 is aligned relative to the ostium 20. The inflation member 46 is then inflated to approximately ten bars pressure while the physician maintains proximal tension on the catheter 36 to inhibit the catheter from slipping into the nose. Preferably, the inflation member 46 first is partially inflated to two bars pressure and the catheter 36 is pulled proximally to place the proximal tapered region 58 at the junction of the lacrimal sac 18 and the upper canaliculus 16 before inflation to ten bars. Dilatation at ten bars pressure is performed for 5-15 minutes, preferably two times for ten minutes each.

Any discomfort experienced with the initial dilatation usually dissipates in a few seconds. Persistent pain may indicate that a portion of the center region 56 is within the canaliculus 16 and the inflatable member 46 should be advanced distally. After dilatation, the catheter 36 and the guidewire 34 are withdrawn. Topical antibiotic, steroid eye drops are given for approximately one week following the procedure.

Instead of bringing the dilatation catheter through the punctum to emerge through the ostium to the nose, the catheter can be advanced in the opposite direction as shown in FIG. 4. This "retrograde" technique is particularly useful when a larger-diameter balloon is required which cannot be advanced through the canaliculus. The dilatation catheter 36a is inserted over the distal end 48 of the guidewire 34 until the distal end 40a of the catheter 36a is positioned proximate to the ostium 20. A hemostat 44 is then clamped to the guidewire 34, and the proximal end 38 is pulled to draw the catheter 36a through the lacrimal sac 18 and the canaliculus 16 with its associated punctum 14. The boundary between the center region 56a and the distal tapered region 60a is indicated by end marker 62. Insertion marker 64 is placed 9-13 mm distal to the marker 62, and preferably at a distance of 10 mm. An additional inflation marker 66 is placed 4-6 mm, and preferably 5 mm proximal to the end marker 62. The distal tapered region 58a lies within the nose. Dilatation is performed using inflatable member 46a as described above in relation to FIG. 3.

A schematic view of a dilatation catheter according to the invention is shown in FIG. 5A. The catheter 70 is a two-lumen catheter having an inflation lumen accessed through leg 76 terminating in luer fitting 78 and a center lumen through which a guidewire may be passed, accessed through leg 72 which terminates in luer fitting 74. The catheter 70 has an overall length A of 62 cm±5 cm and a length B distal to sleeve 80 of 46 cm±2.5 cm. The main shaft 82 has a diameter D of 0.044 inch and is preferably made of high density polyethylene. The center region 84 of the balloon 86 has a diameter when inflated of 4.0 mm at 5 bars pressure and a length E of 8 mm which is indicated at both the distal and proximal ends by distal marker 88 and proximal marker 90, respectively. Inflation marker 92 is located approximately midway between markers 88 and 90. The catheter 70 further includes proximal insertion markers 94 and 96 which are located approximately 10 mm and 15 mm proximal to the proximal marker 90. The distal tip 98 of the catheter 70 has an outer diameter of approximately 0.68 mm (0.027 inch).

Figure 5B:
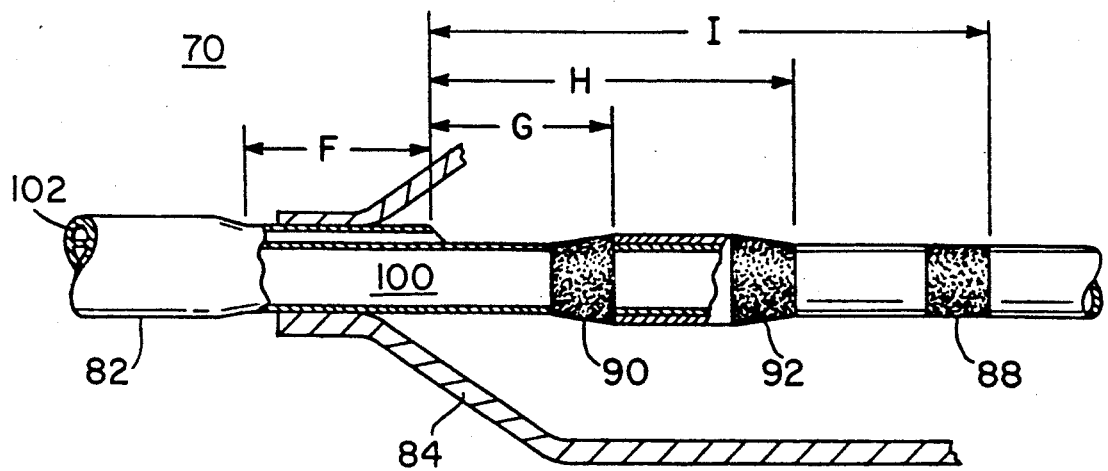
FIG. 5B is an enlarged view of the visually perceptible markings of the invention underlying the balloon.

A portion of the distal end of the catheter 70 is shown in greater detail in FIG. 5B. The center lumen 100 and balloon inflation lumen 102 of shaft 82 are illustrated in partial cross-section. Dimension F indicates a reduced-diameter region at which the proximal end of the balloon 84 is attached, and dimensions G, H and I indicate the distal end of the markers 90, 92 and 88, respectively. In one embodiment, dimension F is 5.5 mm±1 mm, dimension G is 3.5 mm±1 mm, dimension H is 7.5±1 mm, and dimension I is 11.5 mm±1 mm. The markers 90, 92 and 88 are 1-1.5 mm wide bands of black permanent indelible ink such as Marabu TPU-73 pad printing ink. The ink is mixed with Marabu TPU-H ink hardener in a ratio of 4:1 and then roll printed on the shaft before the balloon 84 is placed over the shaft. Except for the shorter length of the balloon 84 and the presence of the visually perceivable markers, the catheter 70 is similar to the "Miniprofile" percutaneous transluminal coronary angioplasty catheter, catalog no. 006480 of USCI. As with the Miniprofile catheter, the shaft is preferably a high density polyethylene.

An alternative catheter according to the invention does not require a separate guidewire. A dilatation catheter 110 according to the invention, FIG. 6, includes 0.014 inch diameter spring coil tip 112, balloon 114, core wire 16, distal outer shaft 118, and proximal shaft 120. The core wire 116 establishes a distal segment which is more flexible than the remaining, proximal segment of the catheter 110. The distal tapering of the core wire 116 and the helical coils of tip 112 provide greatest flexibility at the distal end of the distal segment to emulate a guidewire. This construction is similar to the catheter in U.S. Ser. No. 303,908, filed Jan. 30, 1989, assigned to C. R. Bard, Inc. and incorporated herein by reference. In this construction, however, the balloon 114 is 4.0 mm±0.2 mm in diameter and 8.0±1 mm in length. The distal end marker 122, the center marker 124, proximal marker 126, and proximal insertion marker 128 are shown as raised for clarity, but again are indelible ink bands applied to the catheter structure, in this example core 116 and outer shaft 118, respectively. The spacing of the markers 122-128 are as described as above in FIG. 5A-5B for dilatation of an ostium after a failed DCR, and are as described below for other procedures. The shaft 118 has an outer diameter K of 0.022 inch. The catheter 110 has an overall usable length of approximately 46 cm and is used to dilate an ostium after failed DCR as described above, except that the catheter can be inserted directly into the angiocath sleeve, or can be used immediately after the metal probe as been inserted and withdrawn.

It is desirable for a catheter according to the invention to have a lubricious coating to facilitate insertion of the catheter into the lacrimal system. A silicone coating bonded to the shaft of the catheter is preferred, such as the coating described in U.S. Ser. No. 370,917, filed June 23, 1989, which is incorporated herein by reference. Alternatively, a topical coating of silicone oil can be applied before insertion. One such topical lubricant is Dow Corning 360 medical fluid available from Dow Corning Corp.

Figure 7:
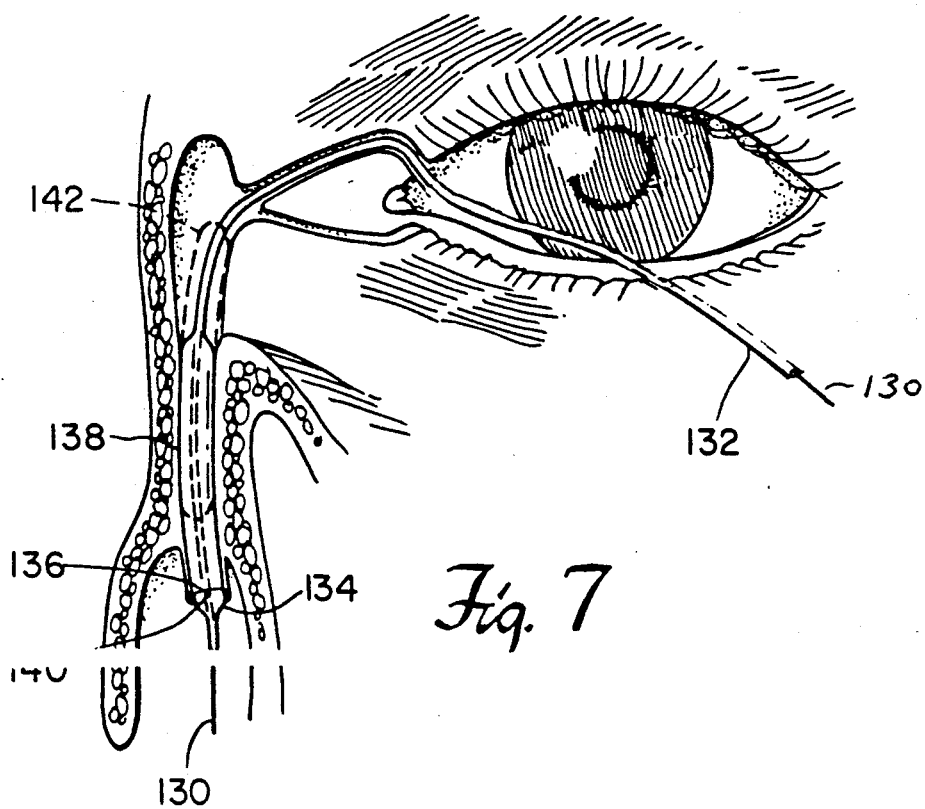
FIG. 7 is a schematic view of the method according to the invention of dilatating the nasolacrimal duct.

A method according to this invention for treating an obstructed nasolacrimal duct is shown in FIG. 7. A guidewire 130 and catheter 132 are inserted as described above, except that the second opening through which the guidewire 130 and the catheter 132 emerge is the natural opening 136 of the nasolacrimal duct 138 rather than an artificially created ostium. A balloon 134 is advanced so that the full-diameter center region of the balloon is visible distal to the opening 136. Preferably, an inflation marker 140 is positioned 4–6 mm proximal to the distal end of the center region for alignment with the opening 136. The balloon 134 is preferably 25–30 mm in length and 3.5 –4.5 mm in diameter for dilatation of an adult nasolacrimal duct which is typically approximately 17 in length. If a shorter balloon is used, a 2-step dilatation procedure is performed in which the balloon is first positioned as shown in FIG. 7, inflated to 10 bars for 8 minutes, and deflated and pulled slightly proximally such that the punctum is aligned midway between two marks which are 9–11 mm and 14–16 mm, preferably 10 mm and 15 mm, respectively, proximal to the proximal end of the center region of the balloon 134. The position of the balloon upon the second dilatation is indicated in phantom by dashed line 142 during the second dilatation procedure. Alternatively, particularly when a larger-diameter balloon is required, the catheter 132 can be directed in a retrograde manner through the opening 136 and then into the nasolacrimal duct 138. The distal end of the catheter 132 in this construction extends at least 15 mm beyond the distal end of the center region so that two insertion markers can be placed at 10 mm and 15 mm distal to the distal end of the center region for alignment with the punctum during the retrograde technique. Additionally, a passage can be established through the medial wall of the lacrimal sac by surgically creating such an opening as described above for DCR.

For treatment of a child, especially 1-2 years old, a smaller, shorter balloon of 2-4 mm diameter and 15-20 mm length appears to be desirable.

A dilatation catheter and method according to the invention can also be used to dilate a narrowed conjunctivodacryocystorhinostomy (CDCR) tract through which a pyrex tube has been placed, or for creation of a new tract after an incision has been made to create such a passage leading from the eye into the nose while bypassing the canaliculi. A metal probe or other instrument is brought through the CDCR from the eye directly into the nose, and then withdrawn. An angiocath having a metal core is brought from the eye side to through the CDCR passage into the nose and the metal core is withdrawn. A guide wire is then brought from the eye side through the angiocath sleeve through the CDCR passage and into the nose. The guidewire is then grasped in the nose and pulled out the external—are after which the angiocath sleeve is withdrawn. The balloon is preferably 4–6 mm in diameter and 15-20 mm in length so that the proximal end of the center region of the balloon remains exterior to the opening by the eye and the distal end of the center region protrudes into the nose. The balloon is inflated at ten bars pressure for two eight-minute periods. The balloon and guidewire are then withdrawn. Alternatively, the balloon may be brought in a retrograde manner over the guidewire from the nose side into the CDCR passage. In either method, a standard stent may then be placed to maintain patency.

Obstruction of a canaliculus can be similarly treated using a balloon having a diameter of 2-4 mm and a length of 15-20 mm for dilating the entire canicular passage, or a shorter length of 4-8 mm for dilating a selected region of the canaliculus. If a DCR has previously been performed, one end of the center region projects external to the punctum while the other end of the center region projects exterior to or is visible through the ostium. If an ostium has not been previously created, the interior end of the balloon resides within the nasolacrimal duct. In the latter case, it is desirable to have two insertion markers spaced 9-11 and 14-16 mm, preferably 10 mm and 15 mm, respectively, from the interior end of the center region for alignment relative to the punctum. In other words, if the catheter is directed from the eye into the nasolacrimal duct, one insertion marker is located 10 mm proximal to the distal end of the center region and a second marker is located 15 mm proximal to the distal end of the center region. The markers will be spaced distal to the distal end of the center region when the catheter is brought in a retrograde manner through the nasolacrimal duct and into the canaliculus.

In an extremely obstructed canaliculus, an ostium is created through DCR and a sterile safety pin or other sharp instrument is passed through the lacrimal sac and into the canaliculus to create a new passage or opening. Standard silicone intubation be installed after dilatation through the canalicular system at the completion of the procedure.

Dilatation can also be performed of the punctum. A balloon is placed through the entire lacrimal system but brought through the punctum so that the ends of the center region project on either side of the punctum. A probe, angiocath, and guidewire are usually not required and the catheter is simply inserted into the punctum and slightly into the canaliculus.

Various changes and modifications to the embodiments shown in the drawings and described above may be made within the scope of the invention. Therefore, it is intended that all matter contained in the above description and shown in the accompanying drawings shall be interpreted in an illustrative and not limiting sense.

What is claimed is:

1. A method of restoring patency to an obstructed portion of the lacrimal system of a patient, comprising:
   providing a catheter having an inflatable member;
   inserting the catheter into the lacrimal system;
   positioning the inflatable member in the obstructed portion of the lacrimal system; and
   inflating the inflatable member to dilate the obstructed portion to restore patencY to the lacrimal system.

2. The method of claim 1 wherein the provided catheter includes a visually perceivable marker having a known spaced relationship to one of the ends of the inflatable member, and positioning the inflated member includes aligning the marker relative to an opening into the lacrimal system.

3. The method of claim 2 wherein the marker is aligned relative to a punctum of the patient.

4. The method of claim 2 wherein the marker is aligned relative to the opening of the nasolacrimal duct into the nose.

5. The method of claim 2 wherein the marker is aligned relative to an ostium formed between the nose and the lacrimal sac.

6. The method of claim 1 wherein the provided catheter includes a lumen for receiving a guidewire, and inserting the catheter includes: passing a guidewire through a first opening into the lacrimal system, through the obstruction, and out a second opening of the lacrimal system; and advancing the catheter over the guidewire.

7. The method of claim 6 wherein advancing the catheter further includes positioning the distal end of the catheter proximate to the first opening, interlocking the proximal end of the catheter relative to the guidewire, and pulling the guidewire to draw the inflatable member into the lacrimal system.

8. The method of claim 6 further including initially passing a probe through the lacrimal system to determine a path between the first and second openings through the obstruction.

9. The method of claim 8 further including withdrawing the probe, installing a sleeve along the path, advancing the guidewire through the sleeve, and withdrawing the sleeve.

10. The method of claim 9 wherein installing the sleeve includes advancing the sleeve with a relatively rigid core along the path, and withdrawing the core while leaving the sleeve in position.

11. The method of claim 1 wherein inflating includes applying fluid under pressure to the balloon for a first period of time, deflating the balloon, and applying fluid under pressure for a second period of time.

12. The method of claim 11 wherein the first and second period of time are between 5-15 minutes each.

13. A method of restoring patency to an obstructed portion of the lacrimal system of a patient, comprising:
providing a catheter including:
   a catheter body having a proximal end and a distal end;
   an inflatable member formed of noncompliant material and disposed proximate to the distal end of the catheter body, the inflatable member having when inflated a center region, a distal tapered region and a proximal tapered region, the distal region attached to the distal end of the center region and the proximal tapered region attached to the proximal end of the center region; and
   at least one visually perceivable marker having a known spaced relationship from one of the distal end and the proximal end of the center region for enabling alignment of the inflatable member with the obstructed portion of the lacrimal system to be dilated;
inserting the catheter into the lacrimal system;
positioning the inflatable member in the obstructed portion of the lacrimal system by aligning the marker relative to an opening into the lacrimal system; and
inflating the inflatable member to dilate the obstructed portion to restore patency to the lacrimal system.

14. The method of claim 13 wherein the provided catheter includes a lumen for receiving a guidewire, and inserting the catheter includes: passing a guidewire through a first opening into the lacrimal system, through the obstruction, and out a second opening of the lacrimal system; and advancing the catheter over the guidewire.

15. The method of claim 14 wherein advancing the catheter further includes positioning the distal end of the catheter proximate to the first opening, interlocking the proximal end of the catheter relative to the guidewire, and pulling the guidewire to draw the inflatable member into the lacrimal system.

16. The method of claim 15 further including initially passing a probe through the lacrimal system to determine a path between the first and second openings through the obstruction.

17. The method of claim 16 further including: withdrawing the probe; installing a sleeve along the path by advancing the sleeve with a relatively rigid core along the path, and withdrawing the core while leaving the sleeve in position; advancing the guidewire through the sleeve; and withdrawing the sleeve.

18. The method of claim 13 wherein the catheter is inserted through a punctum and associated canaliculus, and then through an ostium formed between the nose and the lacrimal sac.

19. The method of claim 18 wherein a first visually perceivable marker is spaced 9-13 mm proximal to the proximal end of the center region, and positioning the inflatable member includes aligning the first marker relative to the punctum.

20. The method of claim 19 wherein the inflatable member is translucent, a second visually perceivable marker is located beneath the inflatable member at a distance of 4-6 mm distal to the proximal end of the center region, and positioning further includes aligning the second marker relative to the ostium.

21. The method of claim 13 wherein the catheter is inserted through an ostium formed between the nose and the lacrimal sac, and then through a canaliculus and its associated punctum, and a first visually perceivable marker is spaced 9-13 mm distal to the distal end of the center region, and positioning the inflatable member includes aligning the first marker relative to the punctum.

22. The method of claim 21 wherein the inflatable member is translucent, a second visually perceivable marker is located beneath the inflatable member at a distance of 4-6 mm proximal to the distal end of the center region, and positioning further includes aligning a second marker relative to the ostium.

23. The method of claim 13 wherein the catheter is inserted through a punctum and associated canaliculus, and then through the nasolacrimal duct.

24. The method of claim 23 wherein the inflatable member is translucent, a first visually perceivable marker is located beneath the inflatable member at a distance of 4-6 mm proximal to the distal end of the center region, and positioning further includes aligning the first marker relative to the opening of the nasolacrimal duct into the nose.

25. The method of claim 24 wherein a second visually perceivable marker is spaced 9-16 mm proximal to the proximal end of the center region, and positioning the inflatable member includes aligning the second marker relative to the punctum.

26. The method of claim 25 wherein the second marker is located 9-11 mm from the proximal end of the center region, and the catheter further includes a third marker located 14-16 mm proximal to the proximal end of the center region, and positioning the inflatable member includes aligning the second and third markers relative to the punctum.

27. The method of claim 26 in which a first dilatation is performed after the first marker is aligned relative to the opening of the nasolacrimal duct, and a second dilatation is performed after aligning the second and third markers relative to the punctum.

28. The method of claim 13 wherein the catheter is inserted through a punctum and associated canaliculus for dilatation of the canaliculus.

29. The method of claim 28 wherein a first visually perceivable marker is spaced 9-16 mm proximal to the distal end of the center region, and positioning the inflatable member includes aligning the first marker relative to the punctum.

30. The method of claim 13 wherein the catheter body of the provided catheter has a distal segment and a proximal segment, the distal segment being more flexible than the proximal segment.

31. The method of claim 30 wherein the distal segment includes a slender, flexible wire.

32. The method of claim 13 wherein the provided catheter includes a lubricious coating to facilitate inserting the catheter into the lacrimal system.

33. The method of claim 32 further including topically applying the coating to the catheter body and the inflatable member.

34. A catheter for dilating an obstructed portion of the lacrimal system of a patient, comprising:
   a catheter body having a proximal end and a distal end;
   an inflatable member disposed proximate to the distal end of said catheter body, said inflatable member having when inflated a center region, a distal tapered region and a proximal tapered region, said distal region attached to a distal end of said center region and said proximal tapered region attached to a proximal end of said center region; and
   at least one visually perceivable marker having a known spaced relationship from one of said distal end and said proximal end of said center region for enabling alignment of said inflatable member with the obstructed portion of the lacrimal system to be dilated.

35. The catheter of claim 34 wherein a first visually perceivable marker is spaced 9-13 mm proximal to said proximal end of said center region for alignment relative to a punctum of the patient.

36. The catheter of claim 35 wherein said inflatable member is translucent and a second visually perceivable marker is located beneath said inflatable member at a distance of 4-6 mm distal to said proximal end of said center region for alignment relative to an ostium formed between the nose and the lacrimal sac of the patient.

37. The catheter of claim 36 in which said inflatable member has a diameter of 3-6 mm when inflated.

38. The catheter of claim 37 in which said inflatable member has a length of 5-10 mm.

39. The catheter of claim 34 wherein a first, visually perceivable marker is spaced 9-13 mm distal to said distal end of said center region for alignment with a punctum of the patient.

40. The catheter of claim 39 wherein said inflatable member is translucent and a second visually perceivable marker is located beneath said inflatable member at a distance of 4-6 mm proximal to said distal end of said center region for alignment relative to an ostium formed between the nose and the lacrimal sac of the patient.

41. The catheter of claim 34 wherein said inflatable member is translucent and a first visually perceivable marker is located beneath said inflatable member a distance of 4-6 mm proximal to said distal end of said center region for alignment relative to the opening of the nasolacrimal duct into the nose.

42. The catheter of claim 41 wherein a second visually perceivable marker is spaced 9-16 mm proximal to said proximal end of said center region for alignment relative to a punctum of a patient.

43. The catheter of claim 41 wherein said inflatable member has a diameter when inflated of 2-5 mm.

44. The catheter of claim 43 wherein said inflatable member has a length of 15-30 mm.

45. The catheter of claim 43 wherein said second marker is located 9-11 mm from said proximal end of said center region and said catheter further includes a third visually perceivable marker located 14-16 mm proximal to said proximal end of said center region.

46. The catheter of claim 34 wherein a first visually perceivable marker is spaced 9-16 mm proximal to said distal end of said center region for alignment relative to a punctum of the patient for dilatation of a canaliculus.

47. The catheter of claim 46 wherein said inflatable member has a diameter of 2-4 mm when inflated.

48. The catheter of claim 34 wherein said catheter body defines a first lumen for inflating said inflatable member and a second lumen for receiving a guidewire.

49. The catheter of claim 34 wherein said catheter body has a distal segment and a proximal segment, the distal segment being more flexible than the proximal segment.

50. The catheter of claim 49 wherein the distal segment includes a slender, flexible wire.

51. The catheter of claim 34 further including a lubricious coating disposed on said catheter body to facilitate inserting said catheter into the lacrimal system.

52. A catheter for dilating an obstructed portion of the lacrimal system of a patient, comprising:
   a catheter body having a proximal end and a distal end:
   an inflatable member formed of noncompliant material and disposed proximate to the distal end of said catheter body, said inflatable member having when inflated a center region, a distal tapered region and a proximal tapered region, said distal region attached to a distal end of said center region and said proximal tapered region attached to a proximal end of said center region;
   at least one visually perceivable dilatation marker disposed within said center region of said inflatable member for enabling alignment of said inflatable member with the obstructed portion of the lacrimal system to be dilated; and
   at least one visually perceivable insertion marker spaced from one of said distal end and said proximal end of said center region for enabling positioning of said inflatable member relative to an opening into the lacrimal system.

* * * * *